US007713351B2

(12) United States Patent
Visuri et al.

(10) Patent No.: US 7,713,351 B2
(45) Date of Patent: May 11, 2010

(54) METHOD FOR CRYSTALLIZATION OF PROTEINS USING POLYSACCHARIDES

(75) Inventors: Kalevi Visuri, Kirkkonummi (FI); Sinikka Uotila, Espoo (FI); Katja Palmunen, Kirkkonummi (FI)

(73) Assignee: Macrocrystal Oy (FI)

( * ) Notice: Subject to any disclaimer, the term of this patent is extended or adjusted under 35 U.S.C. 154(b) by 844 days.

(21) Appl. No.: 10/587,738

(22) PCT Filed: Jan. 11, 2005

(86) PCT No.: PCT/FI2005/000011

§ 371 (c)(1),
(2), (4) Date: Jul. 27, 2006

(87) PCT Pub. No.: WO2005/073245

PCT Pub. Date: Aug. 11, 2005

(65) Prior Publication Data

US 2007/0191590 A1    Aug. 16, 2007

(30) Foreign Application Priority Data

Jan. 28, 2004    (FI) .................................. 20040116

(51) Int. Cl.
*C30B 29/54* (2006.01)
(52) U.S. Cl. .............................. 117/68; 117/69; 117/70; 117/925; 117/926; 117/927
(58) Field of Classification Search .................. 117/68, 117/69, 70, 925, 926, 927
See application file for complete search history.

(56) References Cited

U.S. PATENT DOCUMENTS

| 6,197,322 B1 | 3/2001 | Dutkiewicz et al. |
| 2002/0001619 A1 | 1/2002 | Goldenberg et al. |
| 2003/0175239 A1 | 9/2003 | Margolin et al. |

FOREIGN PATENT DOCUMENTS

| EP | 0 263 490 | 4/1988 |
| JP | 7-258972 | 10/1995 |
| WO | WO 99/55310 | 11/1999 |
| WO | WO 01/76562 | 10/2001 |

OTHER PUBLICATIONS

Jen, et al., "Diamonds in the Rough: Protein Crystals from a Formulation Perspective," Pharmaceutical Research, vol. 18, No. 11 (Nov. 2001), pp. 1483-1488.
Pechenov, et al., "Injectable controlled release formulations incorporating protein crystals," Journal of Controlled Release, 96, (2004), pp. 149-158.
International Search Report dated May 11, 2005.

*Primary Examiner*—Robert M Kunemund
(74) *Attorney, Agent, or Firm*—Ostrolenk, Faber, Gerb & Soffen, LLP

(57) ABSTRACT

The objective of the invention is a crystallizing method for macromolecules, especially proteins and polypeptides, in which selected polysaccharides of biological origin, such as alginate, pectin, dextrin or chitosan and hydrolysates thereof, are used as reagents. Sedimentation of the crystals can be prevented and thus the uniformity of the product contributed with the method. The method can be used to prepare new crystal forms of the polypeptide and to improve the stability of crystals.

11 Claims, 14 Drawing Sheets

METHOD FOR CRYSTALLIZATION OF PROTEINS USING POLYSACCHARIDES

CROSS REFERENCE TO RELATED APPLICATION

The present application is a 35 U.S.C. §§ 371 national phase conversion of PCT/FI2005/000011, filed 11 Jan. 2005, which claims priority of Finnish Application No. 20040116, filed 28 Jan. 2004. The PCT International Application was published in the English language.

PRIOR ART RELATING TO POLYMERS

Chitosan, alginate and pectin are widely used in various applications of biotechnology. Plenty of literature including review type is found of the use of these polymers. Part of the publications concerns, the use of the polymers in question in general (Hirano 1996), whereas others focus on particular application area such as product development of drugs (Borchard and Junginger 2001; Singla and Chawla 2001; Tonnesen and Karlsen 2002).

The electrolyte nature of these polymers enables preparation of physical hydrogels with ions of opposite charge (Hoffman 2002). For example, alginate has been traditionally used as an additive in drug formulations because of the gel forming and stabilizing properties thereof. Alginate and pectin are polyanions and chitosan is a polycation. Biodegradable gels formed of these can be used, for example, in such drug formulations which regulate drug release is in particular conditions in the body, such as in the acid environment of the stomach (Bodmeier, Chen and Paeratakul 1989; el Fattah et al. 1998) or locally in particular tissues such as in articular cartilage (Mierisch et al. 2001). Solutions which will form gel only after administration in body for example due to body temperature (Chenite et al. 2000) or in the acid conditions of the stomach (Miyazaki, Kubo and Attwood 2000) can be prepared of those polymers.

Calcium ion has most commonly been used to gel alginate and pectin. Among other reagents, tripolyphosphate has been used to gel chitosan (Bodmeier, Chen and Paeratakul 1989; Janes, Calvo and Alonso 2001).

Numerous publications concerning the physicochemical properties, viscosity and gelling of these polymer solutions are found in the literature (Desbrieres 2002; Li and Xu 2002; Singla and Chawla 2001). Interest in the research of especially chitosan gels has been increasing during last years. The viscosity of chitosan solution increases with increasing chitosan concentration and deacetylation degree and decreasing temperature. However, chitosan is non-soluble in alkaline and neutral pH, which may occasionally set limits to the use of it as such.

Gels prepared of chitosan and the properties and applications thereof have been studied much when developing various pharmaceutical formulations and therapies. For example, injectable chitin gel has been prepared by acetylating chitosan (Gérentes et al. 2002). Because of still increasing interest there has been discussion about standardization and directions (Dornish, Kaplan and Skaugrud 2001) associated with the safe medical use of chitosan and alginate.

It is generally known in the literature that chitosan, alginate and pectin have been used in various forms of particles as carriers of drug substances and proteins. For example, such orally administered formulation which is controlling drug substance release in which the mixture of chitosan and drug substance is granulated or pelleted has been patented (Säkkinen and Marvola 2001 patent WO0176562). Also the ion complex formed by chitosan and alginate has been used in similar tablets (Takeuchi et al. 2000).

Particles or crystals of drug substances have also been encapsulated in small microspheres which usually have been hardened by dropping the drug substance containing polymer solution dropwise into solution containing the counter-ion (Bodmeier, Chen and Paeratakul 1989; Bodmeier and Paeratakul 1989; Takka and Acartürk 1999). Chitosan has also been encapsulated as an ion complex in glycine solution (Kofuji et al. 2001).

Correspondingly encapsulation of cells (Serp et al. 2000) as well as proteins has been performed. For example, albumin has been encapsulated in chitosan coated pectin particles in calcium chloride solution (Kim et al. 2003). Protein encapsulation has also been performed by incubating protein solution in semi-finished polymer capsule suspension, whereupon the gel contained by the capsules has been filled with protein. Tiourina and Sukhorukov (2002) have demonstrated that α-chymotrypsin enzyme has preserved its activity in such suspension of alginate-protamin capsules. Also the encapsulation of protein crystals in polymer carrier is already known in the prior art (Margolin et al. 2003 patent US2003175239).

In addition to gel or particle forming properties, alginate and chitosan or modifications thereof have been mentioned to have several other advantageous properties, such as antioxidative (Schmidt 2003; Xue et al. 1998) and antimicrobial (Huard et al. 2001 patent U.S. Pat. No. 6,197,322; Jumaa, Furkert and Muller 2002; Kim et al. 1999; Sakurada 1995 patent JP7258972) effects. Because of these properties especially chitosan has been proposed to be used among other things as preservative or therapeutic material for treating skin and curing wounds. Chitosan has been observed to accelerate the curing of wounds by promoting the formation of new skin tissue (Singla and Chawla 2001) and activating the defence mechanisms of the body, such as macrophages (Ueno, Mori and Fujinaga 2001).

Cation nature gives chitosan a special property related to bioadhesion which has been utilized in developing drugs for mucosal administration, containing for example insulin or other macromolecule, peptide, protein or DNA (Fernandez-Urrusuno et al. 1999; Janes, Calvo and Alonso 2001; van der Lubben et al. 2001; Takeuchi, Yamamoto and Kawashima 2001; Thanou, Verhoef and Junginger 2001).

Various applications of these polymers are found a lot, in addition to pharmaceutical industry, in food, cosmetic, textile and paper industry. Chitosan has promising future prospects, not only as gel or additive, but also as biologically active substance.

Prior Art and Summary of the Invention of Protein Crystallization

Some data of protein crystallization has been published as early as the 19th century. Crystallization of haemoglobin is described in a textbook of medicine from the year 1853. Protein crystallization grew in 1920s into rapidly extending use. In the beginning of 20th century crystallization was used particularly in purification of proteins in preparative scale. Over the past decades protein crystallization has been developed primarily for studying molecular structures. Good overviews of protein crystallization methods and used reagents have been published in books edited by Alexander McPherson (1989), A. Ducruix and R. Giege (1992) and Bergfors, T. M. (1999).

The usage of crystallization for production and medical purposes has proportionally decreased while chromatographic purification of proteins has strongly developed.

Lately new interest has arisen towards protein crystallization method for medical formulation.

However, most crystallization methods used nowadays in structure research are not suitable at all for manufacturing medical products. Crystallization reagents used in these methods are physiologically unsuitable and often even toxic. Therefore reagents which are as such compatible for an organism and approved in accordance with pharmacopoeia must be chosen for pharmaceutical crystallizations. Some agents are approved for subcutaneous or intravascular injection, some only for use via digestive tract.

Therefore pharmacological acceptability considerably limits the selection of the agents usable in crystallization. In the following, some basic types of agents or conditions are listed and their suitability for pharmaceutical use is considered.

Inorganic salts, such as ammonium sulphate, sodium sulphate, phosphates, lithium chloride, sodium chloride and potassium chloride are used often as very strong 0.5-3 M solutions which are not pharmacologically acceptable. Alcohols and organic solvents, such as methanol, ethanol, isopropanol and acetone are good crystallizers but toxic. Synthetic polymers, such as numerous different polyethyleneglycols and derivatives thereof are limitedly suitable products of synthetic chemistry. In addition to these examples, thousands of different reagents and combinations thereof have been used for protein crystallization. Very few of these reagents are suitable for medical use or food processes.

In the literature it is generally claimed that protein crystallization is difficult and requires very high purity of the protein. All the foreign agents, especially other proteins and polymers must be removed from the protein solution for crystallization to succeed at all. In accordance with this general principle the protein to be crystallized is purified very thoroughly for example with several successive chromatography methods. After the purification some above mentioned reagent is added whereupon the protein may crystallize. Tens of thousands methods like this have been published in the scientific literature.

Crystallizations of exemplary proteins used in the present invention have been described in the literature thoroughly. Abel published (1926) the first crystallization of insulin. Later Scott (1934) and Schlichtkrull (1956 and 1960) have published several researches of crystallization of insulin. The crystallization of glucose-isomerase has been described in patents by Visuri (1987 and 1992) and in scientific publication by Vuolanto et al. (2003). Törrönen A. et al. (1994) have described the crystallization of xylanase.

Crystallization in Gels

Preparation methods in gel for single large protein crystals needed in x-ray crystallography have been described in their publications by Robert, M. C. ja Lefauchcheux, F. (1988) and Robert, M. C. et al. (1992). With the described methods proteins are crystallized together with silica gel or agarose gel. In these methods gels do not act as a crystallization reagent but on the contrary their role is primarily to control and slow down too fast formation of crystals. The crystallization of proteins is performed by adding crystallization reagents into the mixture in accordance with prior art.

Differences Between the Present Invention and Prior Art and Summary of the Invention In the prior art said polymers are used generally to the encapsulation or stabilization of protein particles or crystals among other things during drying. The present invention relates only to such a method and product form which are based on gel or solution of polymers. The objective of the method of this invention is not to encapsulate proteins, but on the contrary the crystals are free as such in the solution of polymer or in continuous uniform gel. Crystal suspensions in accordance with the invention are not dried.

Crystallizations of proteins or polypeptides performed with polymer solutions or gels thereof in accordance with the present invention are not known in the prior literature. Non-capsulated product in accordance with the invention is, as such, useful uniform mixture of crystalline macromolecule and viscous solution or gel, which can also be stored as being uniform without mixing and can be fed with moderate pressure through a capillary.

The objectives in accordance with the invention are mixture conditions in which the natural properties of the proteins remain unchanged. This objective is promoted by the fact that the physical environment of the crystalline protein is very similar to the environment of the soluble protein.

The present invention differs in its essential parts from the prior art in which gels are used as a tool in crystallization. With the known methods in question the proteins are tried to be crystallized very slowly so that as few crystal nuclei as possible are formed. Then single large crystals are able to form. In the described methods two separate phases of the gel and protein solution are formed which are in contact with each other. In these techniques crystallization is brought about specifically by adding previously known reagent that causes the crystallization of protein into the gel phase. Crystallization takes place slowly when reagent and protein are mixed by diffusion. Gel forming agents in the prior art are different than the polymers which are in accordance with the present invention.

In the technique described in the literature the agents used for gel formation do not act independently as crystallizing reagents. They are specifically desired to be as inert as possible and reacting with the protein to be crystallized is considered as a disadvantage.

In accordance with the present invention the polymers and the protein to be crystallized are mixed rapidly with each other and the crystallization occurs evenly in the whole mixture. Optionally previously formed crystals are mixed with these polymers. Gel formation is not essential prerequisite to the utilization of this technique.

In accordance with the present invention polymers can be essential agents in the formation of crystals. In many of the following examples polymer or hydrolysate thereof is absolutely essential reagent in producing crystals. It can be concluded that these polymers take part in the crystallization in many ways. This conclusion is supported among other things by the surprising observation that in polymers, completely different shape and in average different size protein crystals are developed than those of the same proteins when crystallized with the prior art.

DESCRIPTION OF THE INVENTION

Figure 1:
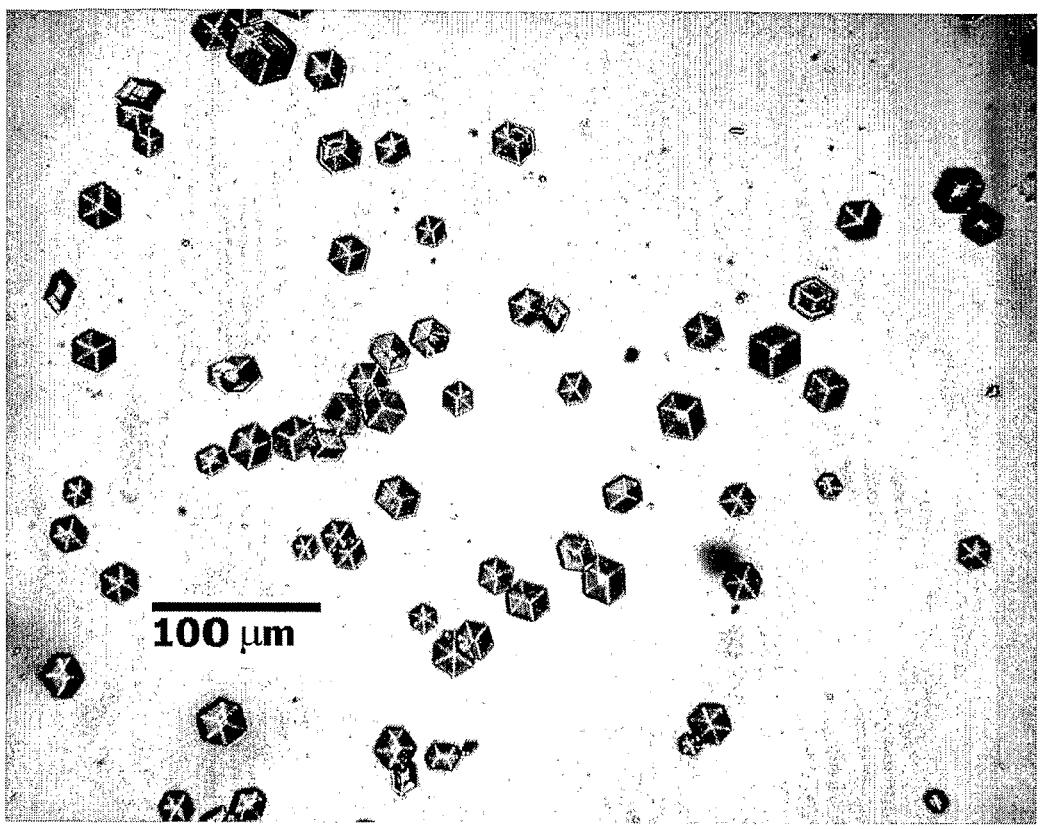
FIGS. 1 to 12 are photographs of crystal made by the examples.

In accordance with the present invention proteins or polypeptides are crystallized in solution containing selected polysaccharides of biological origin. Polymers in accordance with the invention are alginate, dextrin, pectin and chitosan. The molecular sizes of the polymers can vary naturally depending on their biological origin and purification process. Similar types of polymers which have very varying molecular sizes are commercially available. In accordance with general view and experience carbohydrates and polysaccharides protect proteins and contribute them remaining soluble.

Now it has surprisingly been observed and experimentally proved that these polymeric substances can promote crystallization of proteins and peptides or can be suitable for using in connection with crystallization. In addition, it has been observed that these polymers can also be partly hydrolyzed to reduce the molecular size. Using polymers in accordance with the invention and hydrolysates thereof, many crystallization conditions can be chosen in which various useful objectives can be achieved. Different types of polymers can also be appropriately combined.

Several different proteins including glucose-isomerase, insulin, xylanase and endoglucanase have been crystallized and blended with polymer solutions in accordance with the invention. Therefore it can be concluded that the polymers in question can be advantageously used in connection with crystallization of numerous different proteins and polypeptides.

It is especially interesting and advantageous that small and uniform size crystals can be prepared. Such a crystal suspension is preferred for example for accurate dosage. Such a crystal suspension is very stable in viscous solution or thixotropic gel.

Smaller molecular size products which are very suitable for protein crystallization have been prepared of these polymers with enzymatic hydrolysis. With hydrolysis the viscosity of the polymer solution can be reduced, which is beneficial for example when the main objective is to crystallize proteins. If required, more concentrated solutions can be prepared from the hydrolysed polymer than from the original polymer.

Original large molecular polymers are preferable to be used when the objective is a gel like product and preventing the sedimentation of the crystals. Polyelectrolyte polymers such as alginate and pectin can be gelled by adding appropriate counter-ions, for example calcium. With polymers the viscosity of the crystal suspensions can be controlled in a wide range. There is plenty of literature of the properties of these polymers as mentioned above in prior art.

Advantages of the Method

Some advantages of the method according to the invention are described in the following.

Polymers as Crystallizing Reagents

These polymers often act as main protein crystallizing reagents, as examples 12-65 indicate. Crystallization does not occur in pure buffer solution in corresponding conditions.

Medical Acceptability

Polymers are medically acceptable agents. Thus crystalline drug products can be prepared, for example, for subcutaneous injection. Crystallization can be performed in very low salt concentration. The only salt in the crystallization can be the dilute buffer solution, for example, phosphate used in adjusting pH. According to the prior art polysaccharides have stabilizing effect on proteins. In the final composition according to the invention, the dry-weight content of the polymer is low, usually less than 5 percent by weight.

Advantages in the Dosage of the Drugs

The use of the crystalline suspensions usually is complicated or limited by the sedimentation of the crystals and the consequential formation of non-homogeneous suspensions. The commercial slow release insulin preparations which always have to be vigorously shaken prior to use are examples of this. Polymers increase the viscosity of the solution and thus sedimentation of the crystals on the bottom of the vessel can be prevented with them. Thus the drug suspension can be maintained homogenous for a long time.

Advantages in the Production and the Dosage of Industrial Enzymes

Several industrial enzymes could be prepared and stored economically in crystalline form if the crystals would not sediment. Industrial enzymes can be stored and used very concentrated as crystal suspensions. Thus significant savings are obtained. Now the advantages of a crystalline product can be taken into use with the method according to the present invention.

Gelling

If required, the polymer can be gelled prior to the crystallization of the protein, in which case the crystallization occurs uniformly even if the batch is kept still. Crystallization conditions can be adjusted so that the combining of the two solutions produces uniform mixture, wherein both the gel formation and the protein crystallization occur after combining without new reagent additions. The viscosity of the gel can be adjusted to the desired level according to the prior art. The viscosity of the gel according to the invention is adequate to prevent the sedimentation of the crystals but at the same time such that the gel can be fed through a thin capillary with moderate pressure.

Slow Solubility

One of the advantages of the crystalline protein compared to the soluble protein is its slower and longer lasting effect due to the solubilization time which it requires. Physical and chemical environment and crystal size affect the solubilization rate of the crystalline protein. If the crystal size is uniform, the solubilization rate is predictable and controllable.

Homogeneous Crystal Size

When the crystallization of a protein or a polypeptide is performed in the presence of soluble or gelled polymer, polymer mixture or polymer hydrolysate, advantageous differences compared to conventional solution can be observed in the crystallization rate or the crystal size and form. Homogenous nucleation which leads to the formation of uniform crystal size can be brought about with the solution or the gel composition according to the invention.

Preferred Embodiment of the Invention

The protein or the peptide to be crystallized is dissolved in buffer salt solution. The preferred buffer is for example dilute phosphate, the concentration of which can be 20-50 mM. In this solution the protein does not have to crystallize. On the other hand, the protein can be crystalline at this stage if it is acceptable or preferable for the final product.

A solution of the polymer according to the invention, for example pectin, dextrin, alginate, chitosan, polymer hydrolysate or any mixture thereof is prepared in water. The preferred concentration range of the polymer is below 10%. More concentrated solutions of the polymers can be prepared of the hydrolysates due to their lower viscosity. In addition to the polymer the solution can contain an agent which facilitates the solubilisation of the polymer, for example, agents such as acetate needed for controlling the acidity.

A uniform mixture is prepared of the solutions of the protein and the polymer. The crystallization of the protein occurs thereafter. The batch is stirred continuously if the viscosity of the mixture is relatively low. If the viscosity is high enough, the batch does not need stirring after combining the solutions.

If desired, an agent which gels the used polymer or adjusts the viscosity on the desired level can be added to this mixture. Such an agent can be, for example, some divalent cation such as calcium ion. An optional gelling agent can be, for example, a polymer with different electric charge. For example, chitosan and alginate can form a suitable polymer pair.

A requirement for the crystallization of a protein or a polypeptide is that after mixing the batch the conditions are controlled. The acidity (pH) of the mixture has to be such that the protein in question can crystallize. The preferred pH is different for each protein. The preferred pH value is obtained by using precisely measured buffer agents in the solutions of the protein and the polymer. The crystallization of the protein may require the use of some special reagent. According to this invention the polymer itself or a hydrolysate thereof can, in many cases, act alone as the main crystallizing agent.

The following examples illustrate closer the functionality and advantages of the invention considered from different starting points and aspects.

EXAMPLES

Example 1

Crystallization of Human Insulin in 1.5% Sodium Alginate Solution

The material to be crystallized was human insulin. This protein is produced by expressing human insulin gene in *E. coli*. Insulin, carrying the Sigma catalogue product number I 0259 was delivered by Sigma. Dry insulin was dissolved 21.1 mg/ml in acid dissolving reagent, which contained 10 mM hydrochloric acid and 3 mM zinc chloride.

Polymer solution of sodium alginate (Fluka 71238) 3% (w/w) was prepared in water. 50 microliters of 4 M potassium sodium phosphate with pH 5.6 was added in 450 microliters of this polymer solution. The buffered alginate mixture was stirred in a test tube mixer and at the same time 500 microliters of insulin solution with protein concentration of 10.6 mg/ml was added. Final conditions in the crystallization batch were: 1.5% sodium alginate; 0.2 M potassium sodium phosphate and 5.3 mg/ml human insulin, which is equivalent to 145 international units (abbreviated IU) per milliliter. The final concentration of hydrochloric acid is then 2.5 mM and that of zinc chloride 0.75 mM. Crystallization was performed at room temperature (25° C.).

Then at first a uniform amorphous white precipitate was formed. The test tube was moved to nutation. In approximately two and a half hours the amorphous precipitate dissolved and fully crystallized fairly uniform cube-shaped insulin crystal group (FIG. 1) was formed. The length of the edge of the cube-shaped crystals was typically 10-15 micrometers by measuring from the photograph (FIG. 1).

Example 2

Crystallization of Human Insulin in 1.5% Calcium Alginate Gel

The crystallizable material was human insulin as in the example 1. The crystallization was performed so that the calcium alginate gel was formed in the final mixture before the crystallization of insulin.

Dry insulin powder was dissolved in 20% (v/v) acetic acid so that the insulin concentration became 16.7 mg/ml. 200 microliters of this solution was diluted by adding 85 microliters of water. 70 microliters of 0.1 M calcium chloride was added to this insulin solution.

The sodium alginate solution was prepared separately by mixing 1.5 milliliters of 2% (w/w) sodium alginate, 140 microliters of 1 M sodium hydroxide and 5 microliters of 0.25 M zinc chloride. The insulin solution containing calcium chloride was added to the alginate solution at room temperature while stirring properly with magnetic stirrer, whereupon the calcium alginate gel was rapidly formed.

Figure 2:
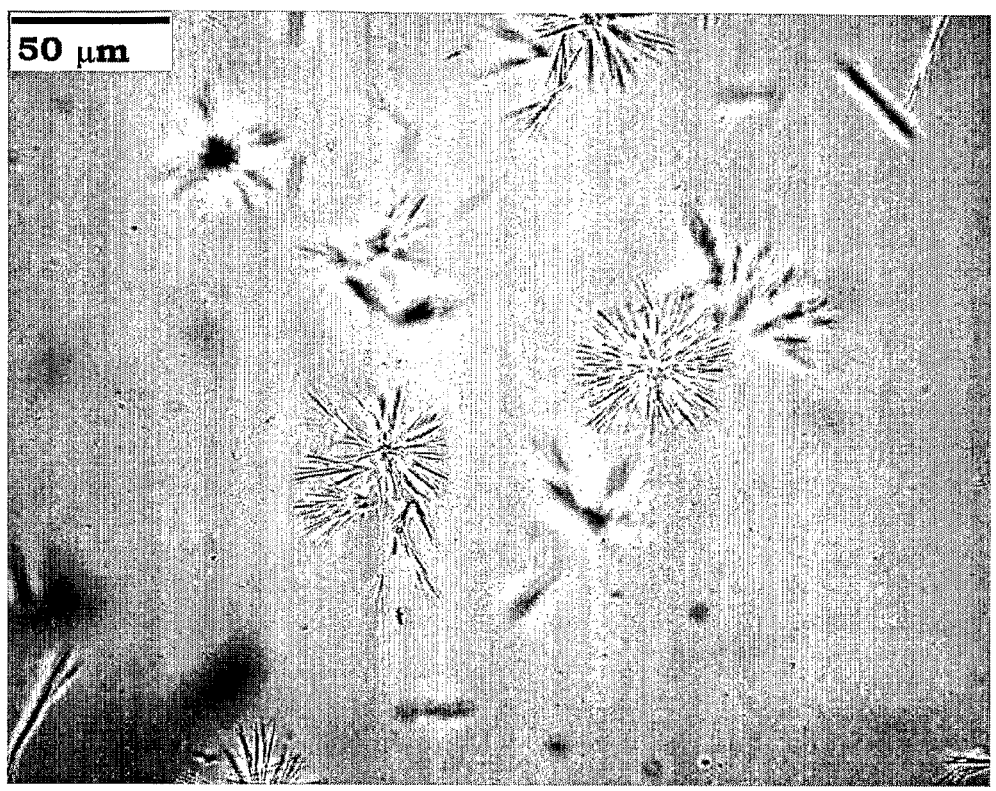

The final crystallization conditions were: 1.67 mg/ml insulin, 2% acetic acid, 70 mM sodium hydroxide, 0.625 mM zinc chloride, 1.5% sodium alginate, 3.5 mM calcium chloride. In this way a clear, fairly homogenous and solid gel which became rapidly cloudy was prepared. The gel was allowed to stand still at room temperature for 3 days. Insulin crystallized as small, uniform size needles and needle bunches (FIG. 2) in the gel (pH 4.1). The typical thickness of the single crystal needles was 1.5 μm and the length 25 μm. The crystals did not sediment in this gel. If the conditions are otherwise the same, but sodium alginate is not added, insulin does not crystallize and the solution remains clear. From this it can be concluded that surprisingly alginate causes the crystallization of insulin.

Example 3

Crystallization of Human Insulin in 0.9% Calcium Alginate Gel

The crystallizable material was human insulin as in the example 2. The crystallization was performed in calcium alginate gel.

Insulin powder was dissolved in 20% (v/v) acetic acid so that the insulin concentration became 16.7 mg/ml. 85 microliters of water and 70 microliters of 0.1 M calcium chloride were added to 200 microliters of this solution. This solution was mixed in 1.645 milliliters of solution containing 85.1 mM sodium hydroxide and 0.76 mM zinc chloride, whereupon the pH of the solution became 4.0.

The mixture was made to a gel by adding 900 microliters of 3% (w/w) sodium alginate solution while stirring with magnetic stirrer. The final crystallization conditions were: 1.15 mg/ml insulin, 1.4% acetic acid, 48 mM sodium hydroxide, 0.431 mM zinc chloride, 0.9% sodium alginate, 2.4 mM calcium chloride.

Figure 3:
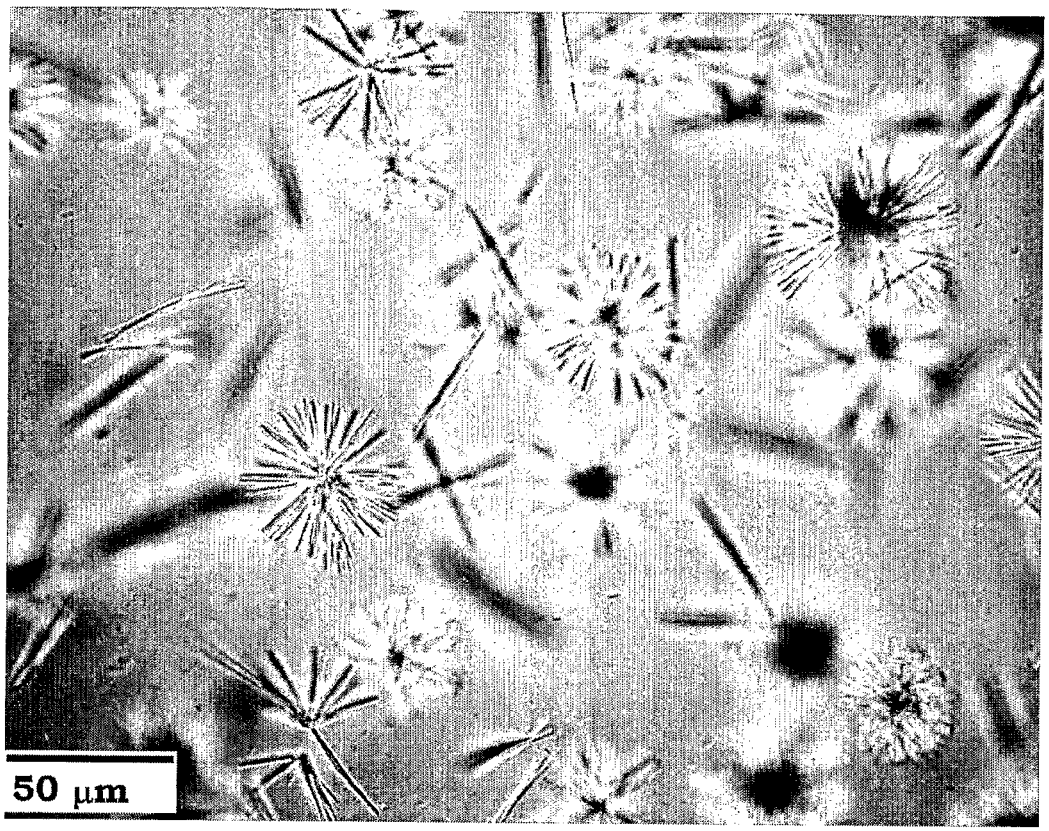

The formed gel was cloudy and less viscous than in the example 2. The gel was allowed to stand still at room temperature for 3 days. Insulin crystallized as small, uniform size needles and needle bunches (FIG. 3) in the gel. The typical thickness of the single crystal needles was 1.5 µm and the length 25 µm. Crystals did not sediment in this gel.

Example 4

Crystallization of Porcine Insulin in 0.45% (w/w) Chitosan pH 5.0

Porcine insulin (Calbiochem) was used as the crystallizable material. As in the example 1, 49 mg of dry insulin powder was dissolved in 4 milliliters of acid dissolving reagent which contained 10 mM hydrochloric acid and 3 mM zinc chloride. 0.9% (w/w) chitosan solution was prepared in 0.28 M acetate buffer with pH 5. The supplier of chitosan was Sigma, in which catalogue insulin has a product number C-3646.

Figure 4:
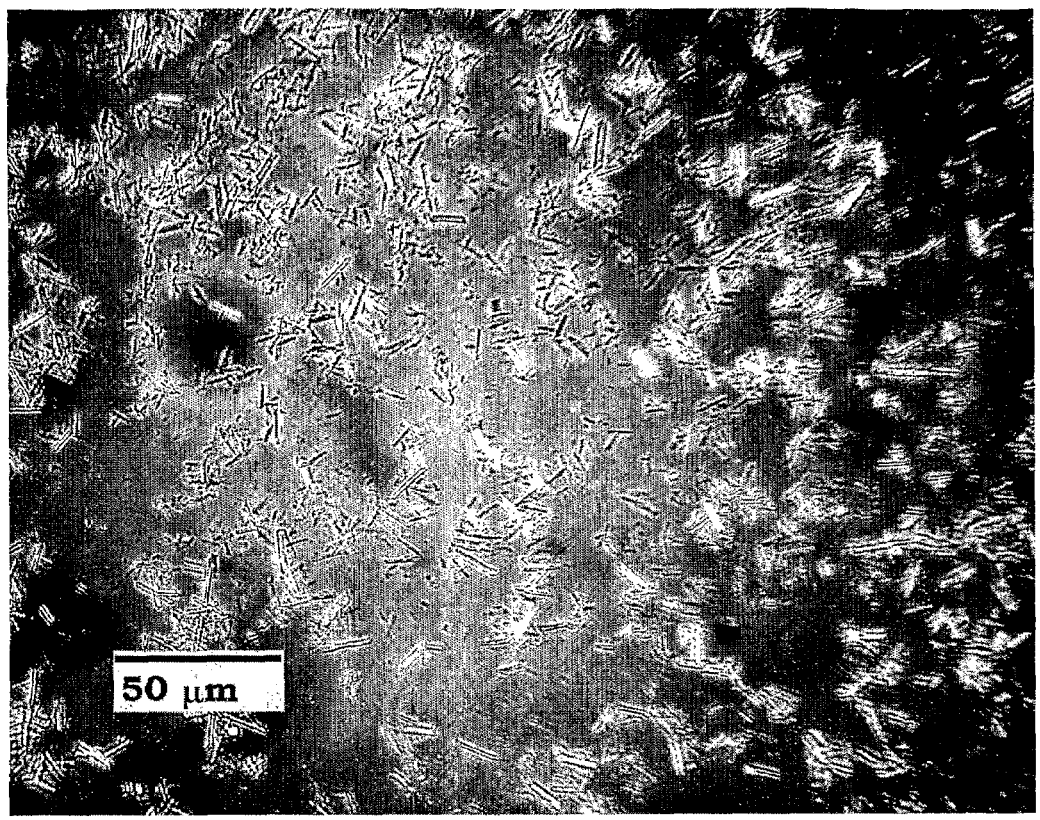

1 milliliter of dissolved porcine insulin was added to 1 milliliter of chitosan solution while stirring all the time with a test tube mixer. After the addition the test tube was transferred to continuous nutation at room temperature. The final conditions in the crystallization batch were: 0.45% (w/w) chitosan, 0.14 M sodium acetate pH 5 and 6.1 mg/ml porcine insulin. The final concentration of hydrochloric acid was 5 mM and that of zinc chloride 1.5 mM. As a result a lot of small rod-shaped crystals were obtained after 24 hours. The crystal yield of the batch was 92.7% of the total amount of insulin. By measuring in the photograph (FIG. 4) the typical length of the crystals was in the range of 5-10 micrometers and the thickness in the range of 0.5-1 micrometers.

Example 5

Crystallization of Porcine Insulin in 0.35% (w/w) Chitosan pH 5.6

A solution of porcine insulin similar to the solution in the example 4 was used in this example. 0.9% (w/w) chitosan solution was prepared in 0.66 M acetate buffer pH 5.6.

100 microliters of dissolved porcine insulin was added to 100 microliters of chitosan solution prepared like this while stirring with a test tube mixer. The final conditions in the crystallization batch were: 0.35% (w/w) chitosan; 0.33 M sodium acetate pH 5.6 and 6.1 mg/ml porcine insulin. The final concentration of hydrochloric acid was 5 mM and that of zinc chloride 1.5 mM. A lot of cube-shaped crystals were formed in this experiment (similar to FIG. 1) in 24 hours. The crystal yield determined by solubility measurement was 98.8%.

Example 6

Crystallization of Human Insulin in 0.45% Chitosan pH 5.0

The same human insulin as in the example 1 was used in the experiment. The powder was dissolved in the same way so that the concentration became 21.1 mg/ml. 0.63% (w/w) chitosan solution was prepared in 0.1 M acetate pH 5.0.

Figure 5:
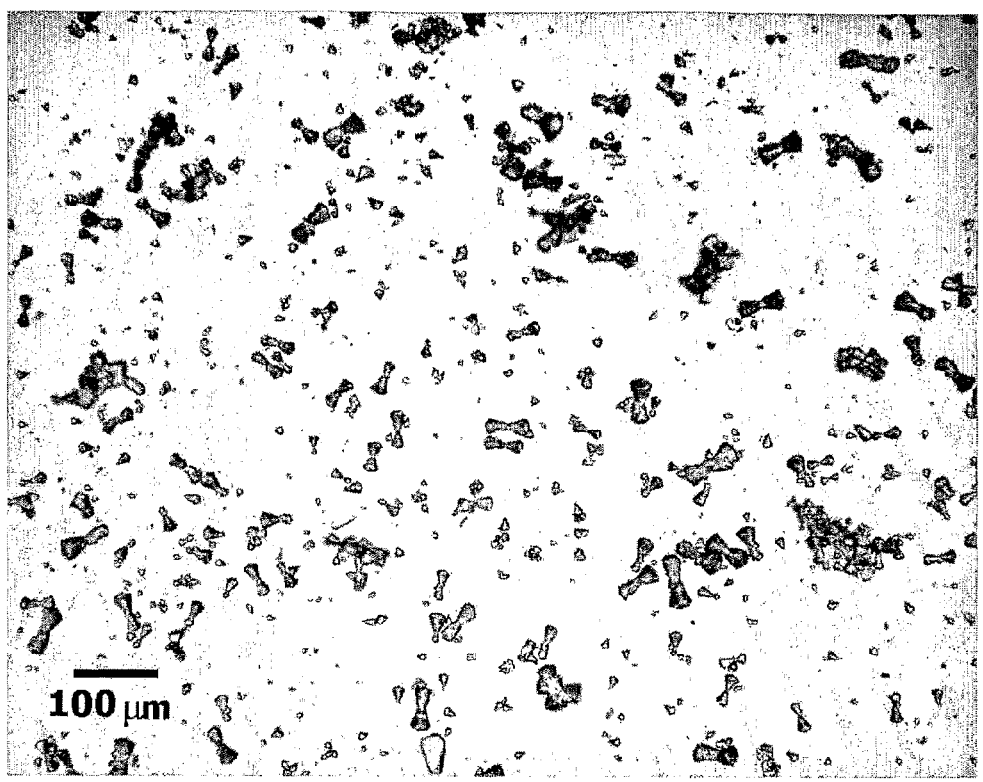

The crystallization batch was prepared by mixing 355 microliters of the chitosan solution and 145 microliters of the insulin solution. The final conditions became: 0.45% chitosan, 0.07 M sodium acetate pH 5.0 and 6.1 mg/ml insulin. The final concentration of hydrochloric acid was 2.9 mM and that of zinc chloride 0.9 mM. As a result a lot of hourglass- and cone-shaped crystals (FIG. 5) which were formed during 24 hours were obtained. The typical length of the hourglass-shaped crystals was 50 µm and the size of the smaller crystal cones was in the range of 10-25 µm. From this it can be observed that chitosan affects surprisingly in the mechanics of the crystal growth consequently producing crystals with completely different shape than those seen after using the methods of prior art.

Examples 7 and 8

Crystallization of Porcine Insulin in the Mixtures of Chitosan and Sodium Alginate:

Example 7

The crystallizable material was porcine insulin. The crystallization was performed in the gel formed by the mixture of chitosan and alginate.

Dry insulin powder was dissolved in the solution containing 0.1 M acetic acid and 3 mM zinc chloride so that the insulin concentration became 12.4 mg/ml. 500 microliters of 1% (w/w) chitosan solution in 0.1 M acetic acid was added to 300 microliters of this solution. 700 microliters of 1.3% (w/w) sodium alginate solution was added immediately to this mixture of insulin and chitosan while stirring properly with magnetic stirrer. In this way a readily flowing clear gel (pH 4.3) was prepared. The gel was allowed to stand still at room temperature for 3 days whereupon insulin crystallized as small needles, the thickness of which was 2-3 µm and the length 30-50 µm. The final crystallization conditions were: 2.5 mg/ml insulin, 0.3% chitosan, 0.6% sodium alginate, 53 mM acetic acid, 0.6 mM zinc chloride, pH 4.3.

Example 8

The crystallizable material was porcine insulin as in the example 7. In this example the concentration of chitosan was significantly higher and that of alginate lower than in the example 7.

The crystallization was performed by mixing two solutions (1) and (2):

Solution (1): 1.4 mg/ml insulin, 0.89% (w/w) chitosan, 0.1 M acetic acid, 0.34 mM zinc chloride. Solution (2): 3.6% (w/w) sodium alginate, 0.48 M sodium hydroxide.

Figure 6:
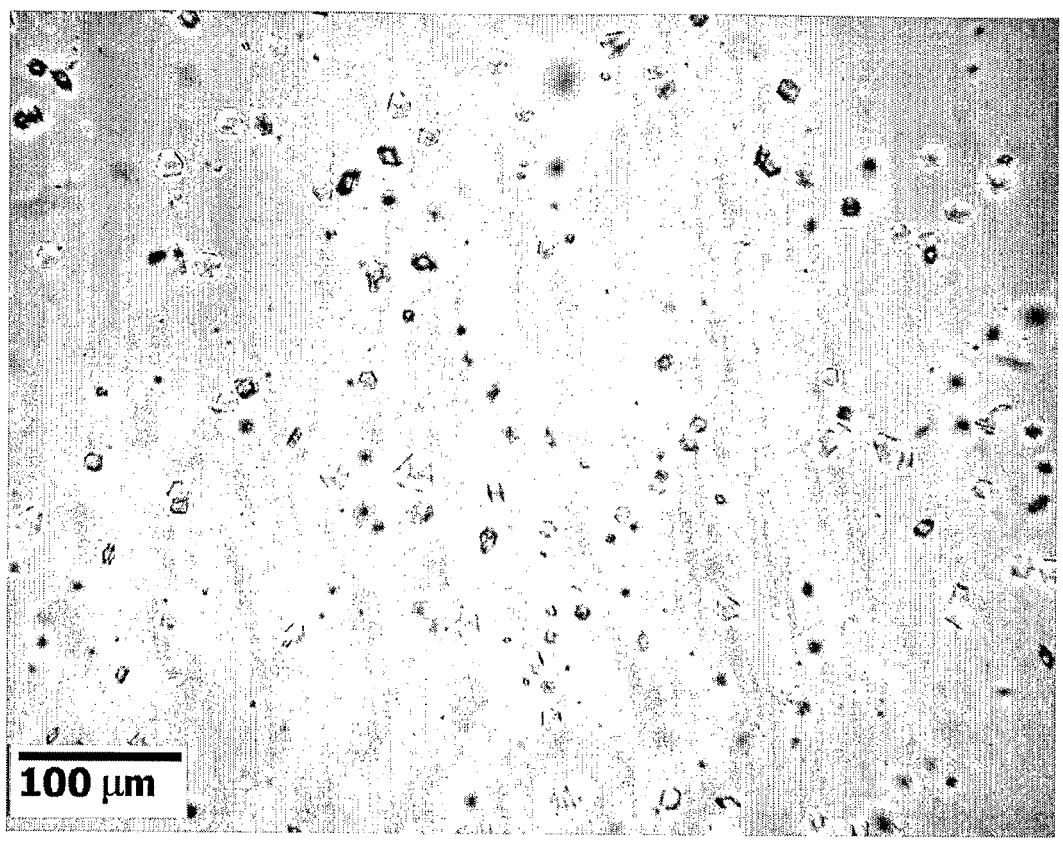

4500 microliters of solution (1) was added to 457 microliters of solution (2) which was stirred thoroughly at the same time. In this way a cloudy gel was prepared which was allowed to stand still at room temperature over night. Insulin crystallized in the gel as small cube- and prism-shaped crystals, the diameter of which was 10-15 µm (FIG. 6). The final crystallization conditions were: 1.3 mg/ml insulin, 0.8% chitosan, 0.2% sodium alginate, 91 mM acetic acid, 44 mM sodium hydroxide, 0.3 mM zinc chloride, pH 5.3.

Examples 9 and 10

Crystallization of Porcine Insulin in the Gel Formed by Glycine and Chitosan

Example 9

The crystallizable material was porcine insulin. The crystallization was performed in the gel formed by glycine and chitosan. Insulin was dissolved in the solution of 0.1 M acetic acid and 3 mM zinc chloride so that the insulin concentration became 12.4 mg/ml. 1.5 milliliters of 1% (w/w) chitosan solution in 0.1 M acetic acid was added to 300 microliters of this insulin solution.

500 microliters of buffer containing 1.05 M glycine and 0.2 M sodium hydroxide (pH 9.0) was added to this solution of insulin and chitosan while stirring properly, whereupon the pH of the solution was 5.5. The formed viscous gel solution was stirred until it was clear and uniform. Thereafter it was allowed to stand still at room temperature, at which time it remained clear for several hours. The next day insulin had crystallized as prism crystals with the diameter of approximately 20 μm. The final crystallization conditions were: 1.61 mg/ml insulin, 0.65% chitosan, 78 mM acetic acid, 0.391 mM zinc chloride, 228 mM glycine, 43 mM sodium hydroxide.

Example 10

Figure 7:
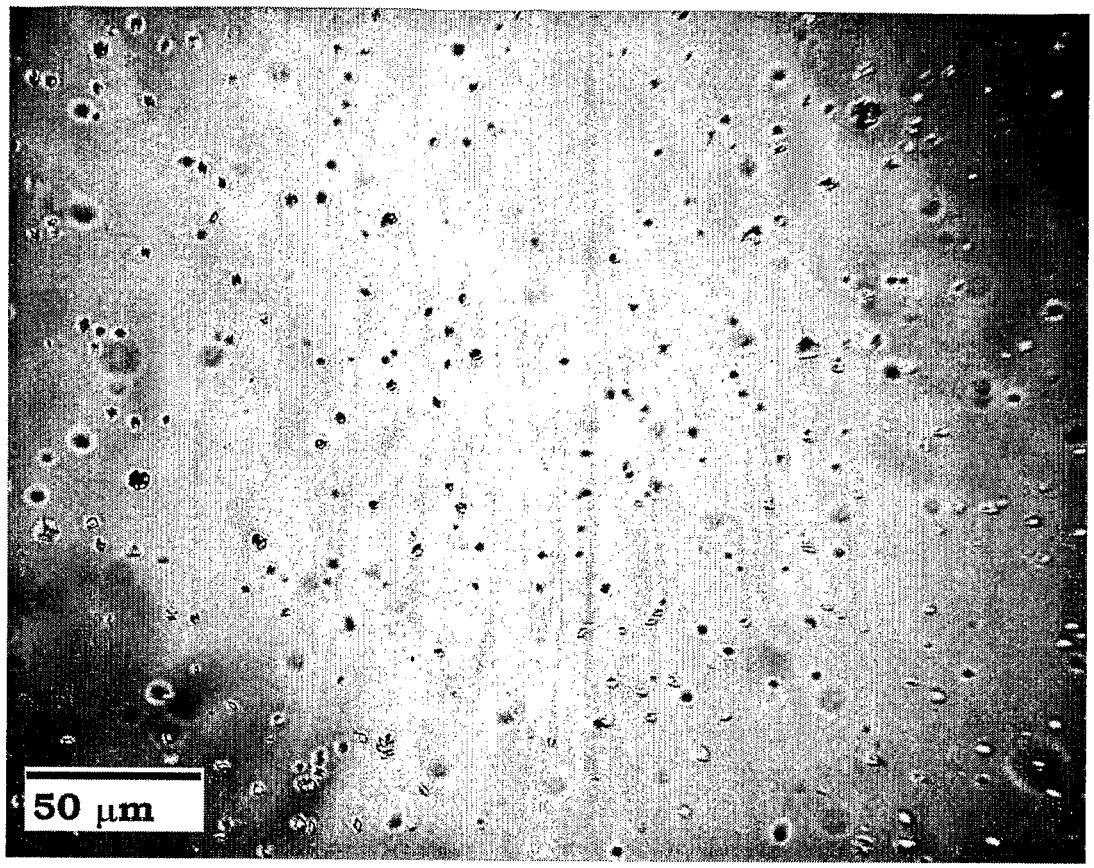

The example 9 was repeated exactly similarly in chemical composition. In this example the crystallization batch of insulin was stirred vigorously, whereupon it turned rapidly cloudy. As a result fairly small prism crystals of insulin with diameter of 4-5 μm were obtained (FIG. 7). The examples 9 and 10 demonstrate that the crystal size in gel can be significantly affected by stirring.

EXAMPLES FOR CRYSTALLIZING OTHER PROTEINS WITH POLYMERS

Example 11

Crystallization of Glucose-Isomerase in Pectin

The crystallizable material was very pure glucose-isomerase diafiltrated in water, the systematic name of which is D-xylose ketol-isomerase EC 5.3.1.5. The crystallization was performed in calcium pectin gel as follows: 1 milliliter of solution of glucose-isomerase (57 mg/ml) in water was pipetted in a test tube. 200 microliters of 0.5 M Tris-HCl buffer pH 7.0 and 800 microliters of 4% (w/w) pectin solution (pectin from citrus peel, Fluka) were mixed in the solution. A clear, homogenous and fairly solid gel was prepared of the solution of pectin and glucose-isomerase by mixing 500 microliters of 1 M calcium chloride in it. The gel was transferred to cold (5° C.), where it was allowed to stand still.

Figure 8:
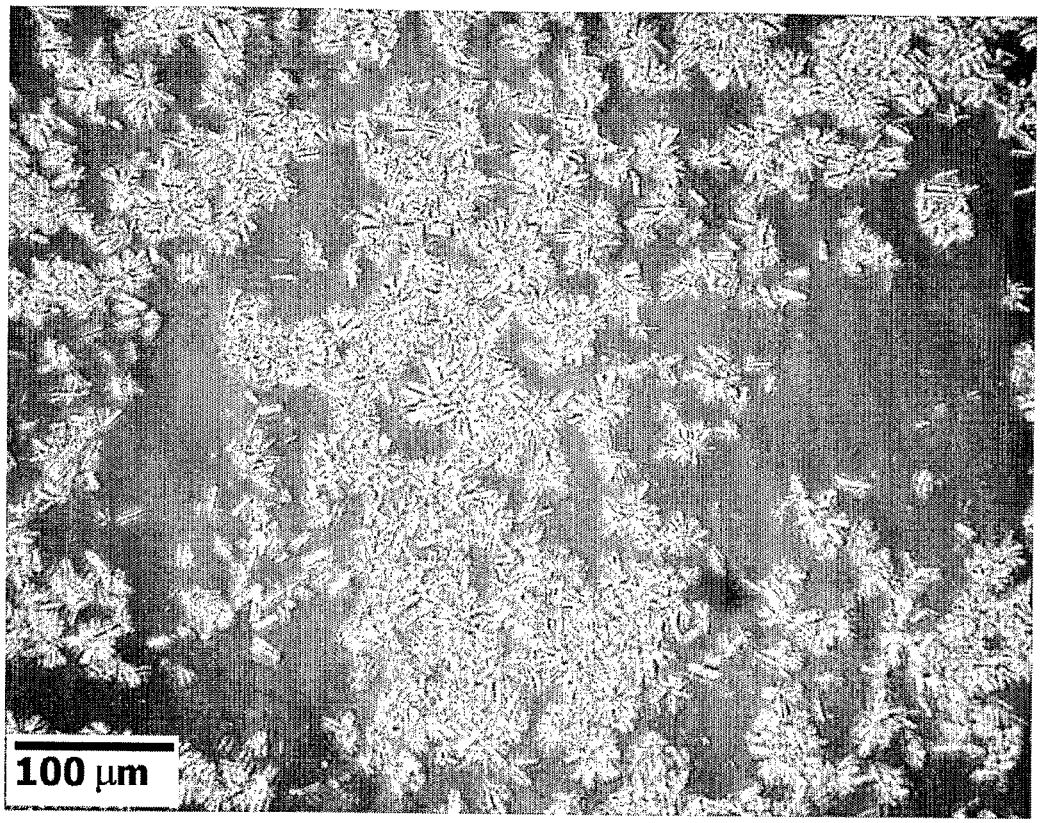

The gel became cloudy within 30 minutes. When observed with microscope, it was noticed that glucose isomerase had crystallized as uniform size rod-shaped crystals. The crystallization was allowed to proceed over night. Photograph (FIG. 8) is taken 20 hours after the start and in it the crystals have average length of 25 μm. The final crystallization conditions were: 23 mg/ml glucose-isomerase, 40 mM Tris-HCl pH 7, 1.3% pectin, 200 mM calcium chloride. The crystals do not sediment in this gel.

Figure 9:
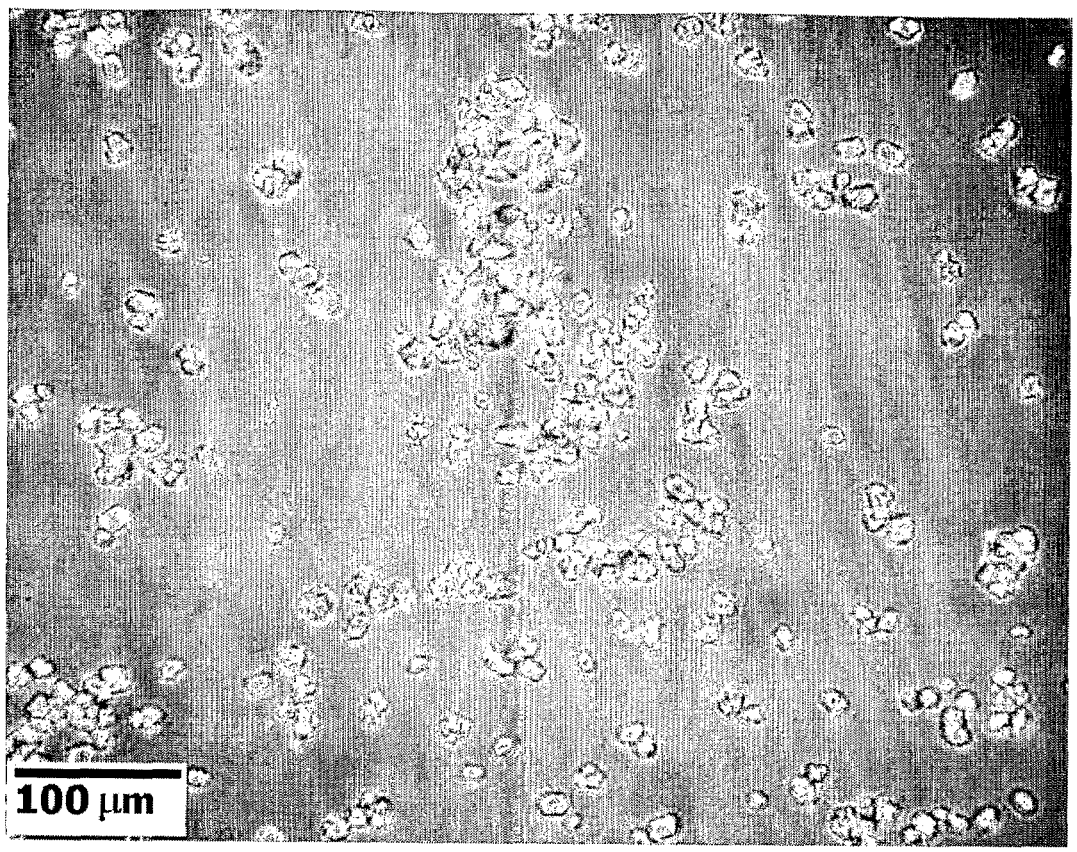

The crystallization of glucose-isomerase is significantly slower and the formed crystals are larger polygons (FIG. 9) if pectin has not been added. Without calcium chloride glucose-isomerase does not crystallize in corresponding conditions.

Examples 12-38

Crystallization of Glucose-Isomerase in Alginate and Alginate Hydrolysate

The alginate hydrolysates suitable as crystallization reagents were prepared with an enzymatic method. The product data of the enzyme used in the example: the name of the enzyme is alginate-lyase, the activity 2630 U/g, production organism *Flavobacterium multivolum*, supplier Sigma, product number A 6973. A water solution of sodium alginate 8% (w/w) was hydrolyzed with alginate lyase at 40 degrees temperature for 20 hours. The hydrolysis was performed to different degrees by using various amounts of enzyme in relation to alginate. The enzyme amounts were 0.9 mg-9.5 mg per gram alginate. Hydrolysis was stopped by boiling the mixtures in water bath for 20 minutes. Thereafter the hydrolysates were filtered with paper to remove the solid matter. The alginate hydrolysates prepared like this were used as solutions having various concentrations to crystallize proteins with the microdiffusion method.

The crystallizable material was very pure glucose-isomerase diafiltrated in water. The crystallization was performed with the microdiffusion method at the temperature of +5° C. by first mixing the reagents so that their concentrations were half of what is reported as a final concentration in the following tables. During each experiment both the protein and the polymer are concentrating due to evaporation of water so that the final concentration reported in the table is obtained. The initial volume of each experiment was 10 microliters and the final volume 5 microliters. Due to this concentrating the conditions change to favorable for protein crystallization.

These examples produced many-sided (for example FIG. 9) or double-pyramid-shaped crystals typical for glucose-isomerase. A similar process can be repeated, if desired, in larger scale by evaporating or with some other usual water removing method.

TABLE 1

Examples 12-38

| Example No | Final concentration of glucose-isomerase mg/ml | Concentration of alginate % | Hydrolysis degree mg enzyme/g alginate | 50 mM phosphate pH | Result |
|---|---|---|---|---|---|
| 12 | 57 | 1 | 0.9 | 6.2 | crystallized |
| 13 | " | 2 | " | 6.2 | crystallized |
| 14 | " | 4 | " | 6.2 | crystallized |
| 15 | " | 1 | " | 8.2 | crystallized |
| 16 | " | 2 | " | 8.2 | crystallized |
| 17 | " | 4 | " | 8.2 | crystallized |
| 18 | " | 1 | 2.4 | 6.2 | crystallized |
| 19 | " | 2 | " | 6.2 | crystallized |
| 20 | " | 4 | " | 6.2 | crystallized |
| 21 | " | 1 | " | 8.2 | crystallized |
| 22 | " | 2 | " | 8.2 | crystallized |
| 23 | " | 4 | " | 8.2 | crystallized |
| 24 | " | 1 | 4.7 | 6.2 | crystallized |
| 25 | " | 2 | " | 6.2 | crystallized |
| 26 | " | 4 | " | 6.2 | crystallized |
| 27 | " | 1 | " | 8.2 | crystallized |
| 28 | " | 2 | " | 8.2 | crystallized |
| 29 | " | 4 | " | 8.2 | crystallized |
| 30 | " | 1 | 9.5 | 6.2 | crystallized |
| 31 | " | 2.5 | " | 6.2 | crystallized |
| 32 | " | 5 | " | 6.2 | crystallized |
| 33 | " | 1 | " | 8.2 | crystallized |
| 34 | " | 2.5 | " | 8.2 | crystallized |
| 35 | " | 5 | " | 8.2 | crystallized |
| 36 | 54 | 1 | not hydrolyzed | 7 | crystallized |
| 37 | " | 3 | not hydrolyzed | 7 | crystallized |
| 38 | " | 5 | not hydrolyzed | 7 | crystallized |

Examples 39-41

Crystallization of Glucose-Isomerase with Pectin

The same glucose-isomerase as in the examples 12-38 was used as the crystallizable protein. The crystallization was performed with the microdiffusion method as in the examples 12-38.

The crystals with 4% pectin from citrus peel, Fluka) were formed at room temperature. The crystals with lower pectin levels 1% and 2% were formed at the temperature of 7 degrees. These examples demonstrate that glucose-isomerase can be crystallized by using pectin alone as a crystallization reagent. In the same conditions in 20 mM phosphate buffer pH 7 without pectin glucose-isomerase does not crystallize.

TABLE 2

Examples 39-41

| Example No | Final concentration of glucose-isomerase mg/ml | Concentration of pectin % | 20 mM phosphate pH | Result |
|---|---|---|---|---|
| 39 | 54 | 1% | 7 | crystallized |
| 40 | " | 2% | 7 | crystallized |
| 41 | " | 4% | 7 | crystallized |

Examples 42-47

Crystallization of Xylanase in Hydrolysates of Alginate

Xylanase was used as the crystallizable material. This xylanase is produced with *Trichoderma* sp organism and is known in the literature by the systematic name of endo-1,4-β-xylanase EC 3.2.1.8. The crystallization was performed with the microdiffusion method at temperature of 5 degrees in hydrolysates of alginate as in the examples 12-38. Xylanase does not crystallize in corresponding conditions without the hydrolysate of alginate. Photograph (FIG. 10) presents typical crystals of xylanase prepared in these examples. The typical crystals are relatively thin plates, which have the thickness of 5-10 μm and length of edges 200-300 μm.

TABLE 3

Examples 42-47

Figure 10:
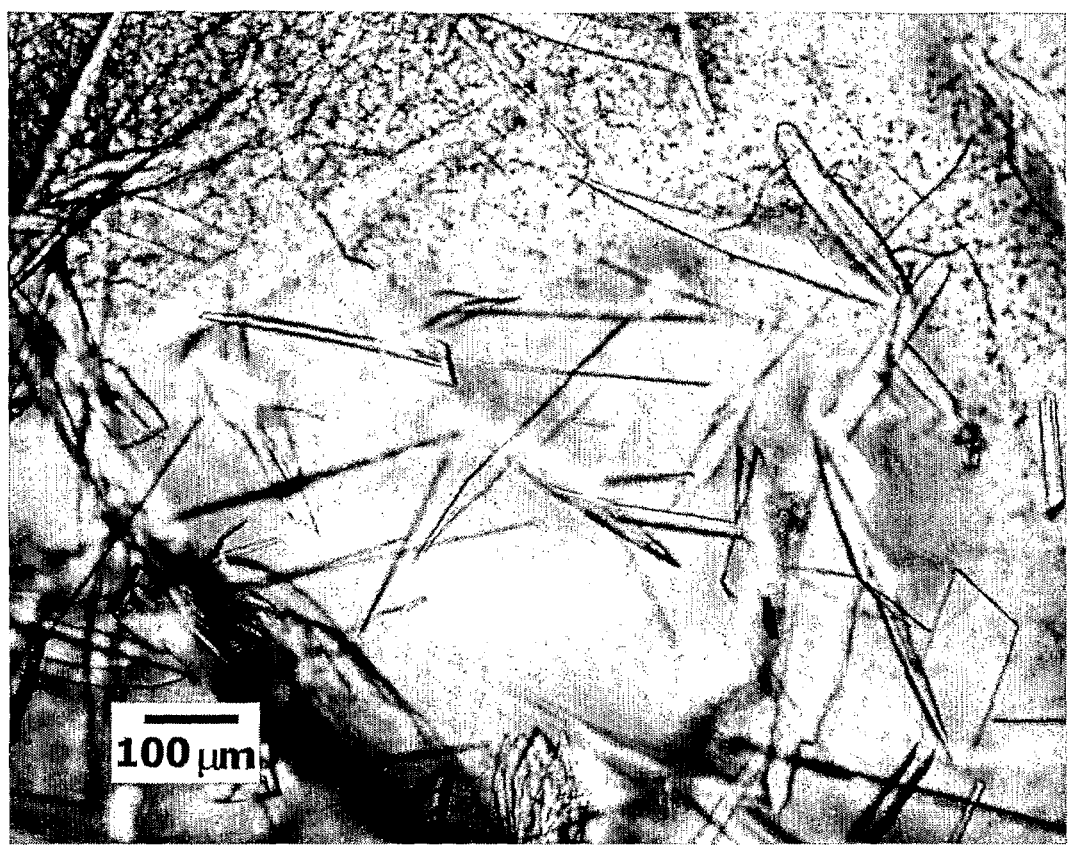

| Example No | Final concentration of xylanase mg/ml | Concentration of alginate % | Hydrolysis degree mg enzyme/g alginate | 50 mM phosphate pH | Result |
|---|---|---|---|---|---|
| 42 | 31 | 1 | 0.9 | 8.2 | crystallized |
| 43 | " | 2 | " | " | crystallized |
| 44 | " | 5 | " | " | crystallized |
| FIG. 10 |  |  |  |  |  |
| 45 | " | 2 | 2.4 | " | crystallized |
| 46 | " | 5 | " | " | crystallized |
| 47 | " | 5 | 4.7 | " | crystallized |

Examples 48-65

Crystallization of Glucose-Isomerase with Hydrolysates of Pectin

A solution of 2% (w/w) pectin was prepared in water. This solution was hydrolyzed at the temperature of 40° C. to different hydrolysis degrees with pectinase enzyme (Genencor International, Multifect PL) by relating the amount of enzyme to pectin dry matter. Two batches were prepared with different degrees of hydrolysis, the other was hydrolyzed only partly and the other nearly to the end. The enzyme amounts were 0.01 mg and 0.1 mg per grain pectin. Hydrolysis was stopped by boiling in water bath for 20 minutes. The pectin solution was filtered clear, cooled and freeze-dried.

The pectins hydrolyzed this way were used in different concentrations to crystallize glucose-isomerase. In corresponding conditions without hydrolysates of pectin glucose-isomerase does not crystallize. The crystallization examples were performed as microdiffusion experiments at the temperature of 6° C. The crystals prepared in the experiments were prisms of good quality, the typical edge lengths of which were 100-200 micrometers. The shape of the crystals appears illustratively in the photograph (FIG. 11).

TABLE 4

Examples 48-65

Figure 11:
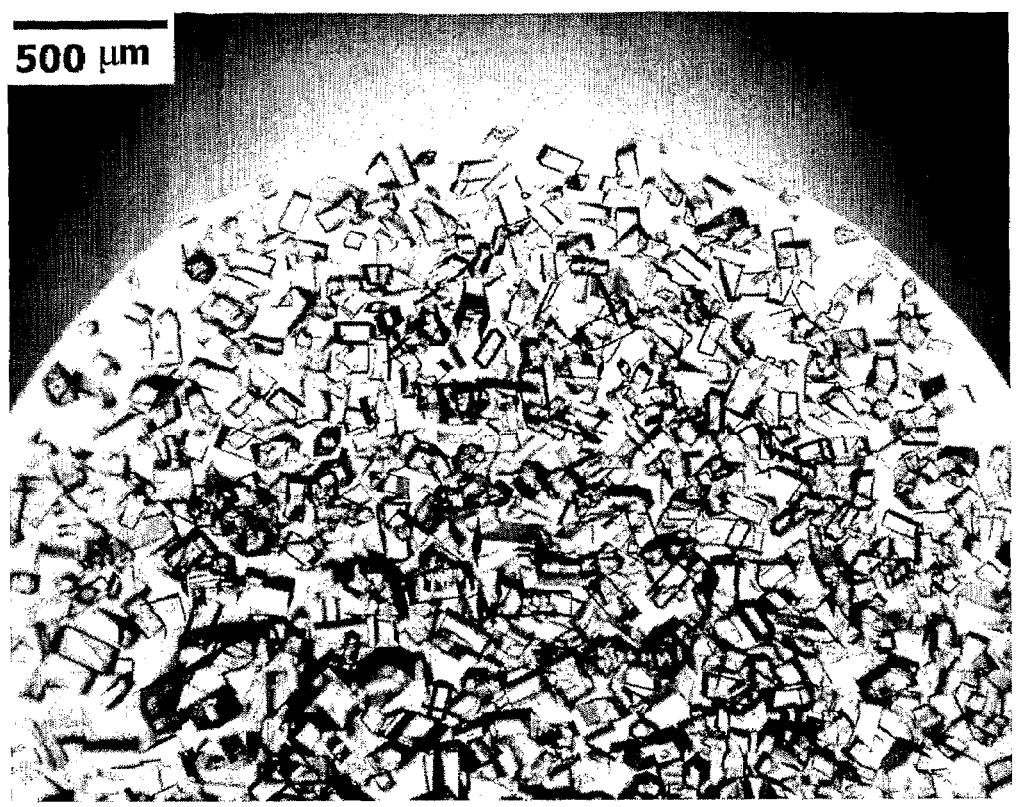

| Example No | Final concentration of glucose-isomerase | Concentration of pectin % | Hydrolysis degree mg enzyme/g pectin | 50 mM phosphate pH | Result |
|---|---|---|---|---|---|
| 48 | 49 mg/ml | 1 | 0.01 | 6.4 | crystallized |
| 49 | " | 3 | 0.01 | 6.4 | crystallized |
| 50 | " | 3 | 0.01 | 6.8 | crystallized |
| 51 | " | 3 | 0.01 | 7.2 | crystallized |
| 52 | " | 3 | 0.1 | 6.4 | crystallized |
| 53 | " | 3 | 0.1 | 6.8 | crystallized |
| 54 | " | 3 | 0.1 | 7.2 | crystallized |
| 55 | " | 5 | 0.01 | 6.4 | crystallized |
| 56 | " | 5 | 0.01 | 6.8 | crystallized |
| FIG. 11 |  |  |  |  |  |
| 57 | " | 5 | 0.01 | 7.2 | crystallized |
| 58 | " | 5 | 0.1 | 6.8 | crystallized |
| 59 | " | 5 | 0.1 | 7.2 | crystallized |
| 60 | " | 9 | 0.01 | 6.4 | crystallized |
| 61 | " | 9 | 0.01 | 6.8 | crystallized |
| 62 | " | 9 | 0.01 | 7.2 | crystallized |
| 63 | " | 9 | 0.1 | 6.4 | crystallized |
| 64 | " | 9 | 0.1 | 6.8 | crystallized |
| 65 | " | 9 | 0.1 | 7.2 | crystallized |

Examples 66-79

Crystallization of Human Insulin in Hydrolysates of Pectin

The crystallization examples were performed as microdiffusion experiments at room temperature with the same technique as the examples 12-38. In many experiments the crystals were formed as soon as in approximately one hour after pipetting in other words before equilibrium state. Thus the conditions at the crystallization moment resembled more a batch experiment than a microdiffusion experiment. The crystals were either small needles and needle bunches or prisms. The typical measures of the crystals presented in the photograph (FIG. 12) were the following: the thickness 1-2 μm and the length 20-30 μm.

TABLE 5

Examples 66-79

Figure 12:
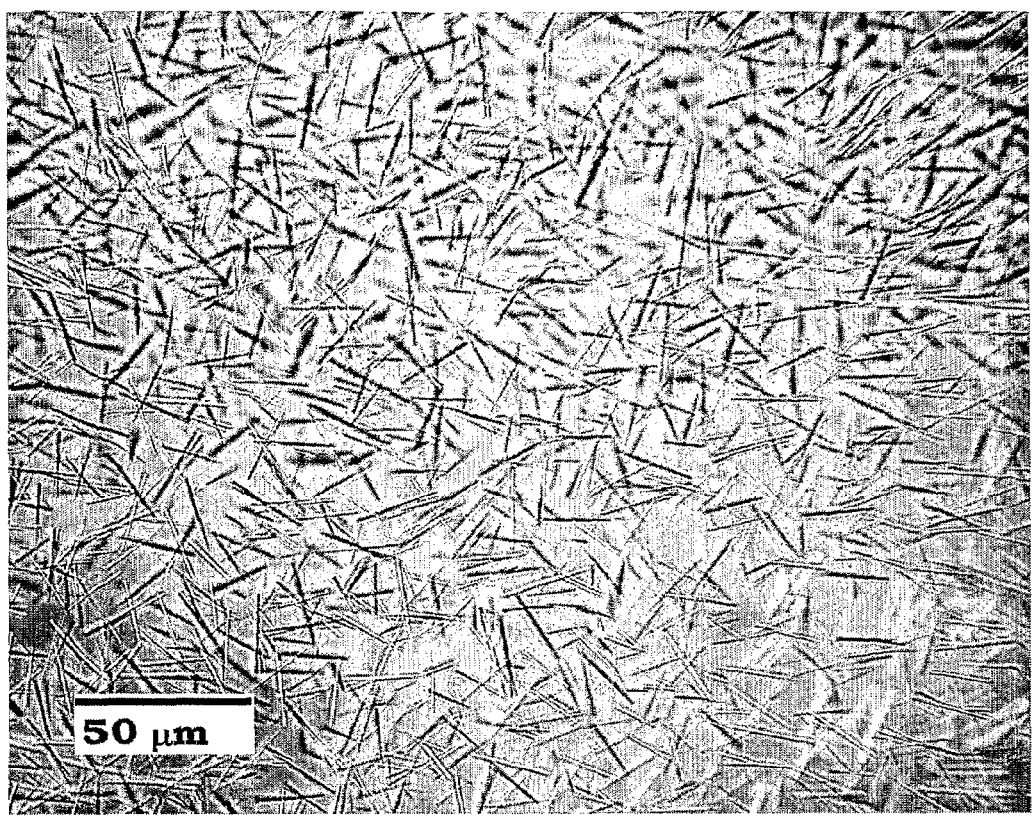

| Example No | Final concentration of insulin mg/ml | Concentration of pectin % | Hydrolysis degree mg enzyme/ g pectin | 50 mM phosphate pH | Result |
|---|---|---|---|---|---|
| 66 | 4 | 3 | 0.01 | 5.0 | crystallized |
| 67 | " | 3 | 0.01 | 7.7 | " |
| 68 | " | 3 | 0.1 | 5.0 | " |
| 69 | " | 3 | 0.1 | 7.7 | " |
| 70 | " | 5 | 0.01 | 5.0 | " |
| 71 | " | 5 | 0.01 | 6.6 | " |
| 72 FIG. 12 | " | 5 | 0.1 | 5.0 | " |
| 73 | " | 5 | 0.1 | 6.6 | " |
| 74 | 2 | 9 | 0.01 | 5.0 | " |
| 75 | " | 9 | 0.01 | 6.6 | " |
| 76 | " | 9 | 0.01 | 7.7 | " |
| 77 | " | 9 | 0.1 | 5.0 | " |
| 78 | " | 9 | 0.1 | 6.6 | " |
| 79 | " | 9 | 0.1 | 7.7 | " |

Examples 80-84

Crystallization of Insulin with Dextrin, Pectin and the Mixture of Sodium Alginate and Pectin Human insulin was used as the crystallizable protein in the following examples. The solution contained 4 mg/ml insulin, 2.5 mM HCl and 0.75 mM $ZnCl_2$. The crystallization examples were performed as microdiffusion experiments at room temperature. Dextrin prepared of corn starch was a product of Fluka no 31412. Sodium alginate and pectin were the same as in the examples 1 and 39-41. Insulin was crystallized with dextrin as plate-shaped crystals whereas the pectin containing solutions crystallized insulin in needle-shaped crystal form.

TABLE 6

Examples 80-84

| Example No | Final concentration of insulin mg/ml | Crystallizing polymer and concentration % | 40 mM phosphate pH | Result |
|---|---|---|---|---|
| 80 | 4.0 | 10% Dextrin 15 | 5.0 | crystallized as plates |
| 81 | " | 20% Dextrin 15 | 5.0 | crystallized as plates |
| 82 | " | 30% Dextrin 15 | 5.0 | crystallized as plates |
| 83 | " | 2% Pectin | 5.0 | crystallized as needles |
| 84 | " | 0.5% Sodium alginate and 1% Pectin | 5.0 | crystallized as needles |

Examples 85-88

The Viscosity of the Gels Containing Crystals

It is a very useful property that the formed mixture of the polymer and the crystals has thixotropic viscosity type. This means that the viscosity of the solution decreases when the shear force increases. From this it follows that when the mixture is stored in a still container, it turns very rapidly into a solid gel, in which the crystals do not sediment. When the mixture is dosed and pumped, it turns into liquid-form and manageable with relatively low force. These properties become apparent in the figure (FIG. 13), in which the mixtures according to the examples 85 and 86 have been pumped with different pressures through a capillary tube. In the figure it becomes apparent that when increasing the pressure the flow rate of the sample through the capillary increases sharply. The flow rate of glycerol which was used as a reference substance increases linearly with increasing pressure. This means that the viscosity of glycerol remains constant in the conditions used in this example.

Figure 14:
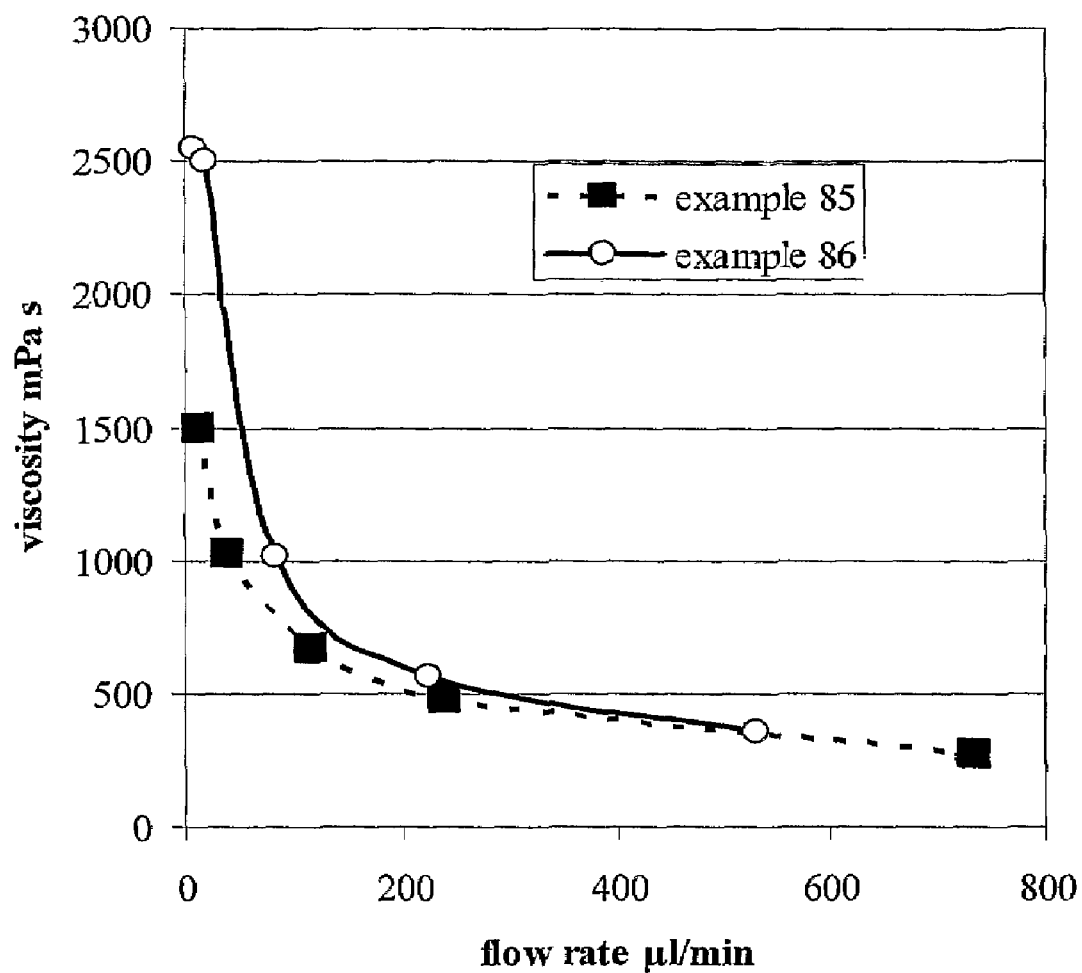

According to the handbook (CRC Handbook of Chemistry and Physics, 1994 CRC Press. Inc.) viscosity of glycerol at room temperature is 934 mPa s. Viscosity of the crystal suspensions at different flow rates was calculated on the basis of viscosity of the reference substance and the figure (FIG. 14) was drawn on the basis of these results. This figure shows illustratively that the viscosity of the example suspensions decreases very sharply when the flow rate increases.

The examples 87 and 88 were prepared so that as high crystal concentration as possible was obtained and that at the same time such a mixture was obtained which can be pumped through a thin capillary, for example, an injection needle. The highest concentration of the protein crystals is essentially determined by the liquid content of the crystals. According to the literature it is known that the crystals of different proteins and peptides contain significantly different amounts of mother liquor, usually water and buffer salts dissolved in water. One gram of solid crystal mass of endoglucanase can contain at the most 358 mg of protein. Therefore the most concentrated solutions of this protein that can be pumped or injected are inevitably more dilute than this. In the examples 87 and 88 samples were prepared, which contained 255 mg and 272 mg of endoglucanase in a milliliter of crystal mixture. Surprisingly it could be observed that the flow rates of these suspensions with low pressures were of the same order than in the examples 85 and 86, in which there was only 17.5 mg per milliliter of endoglucanase. These suspensions were thus very easily injectable. However, the suspensions turned into solid gels within an hour after the stirring was stopped. The gels can be turned fluid again by stirring with very low force The examples 87 and 88 demonstrate that when the concentration of the protein crystals is increased, the requirements for gelling agent calculated for the whole mixture is decreasing. This can be understood so that the polymer can exist only in the liquid space between the crystals which reduces when the proportion of the crystals increases.

Example 85

Figure 13:
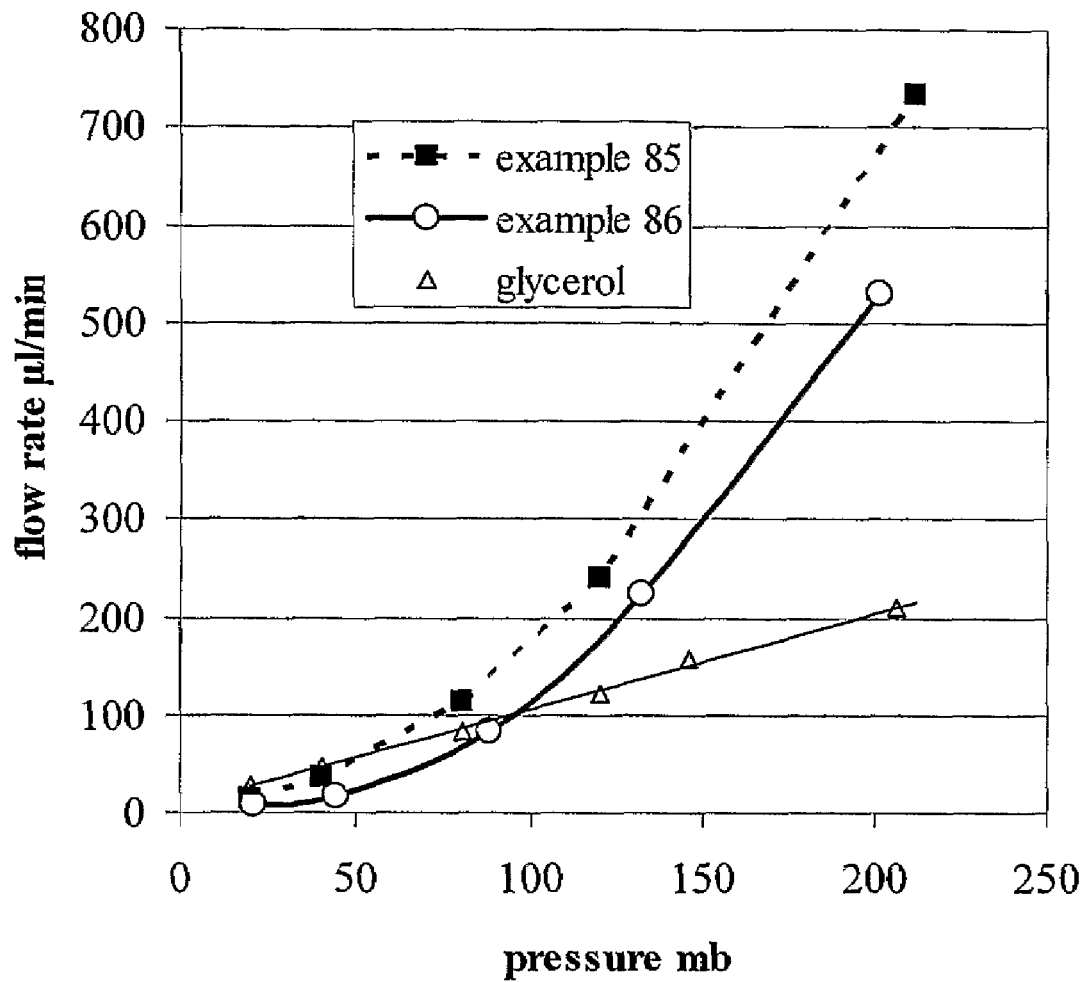
FIGS. 13 and 14 show pressure versus flow rate in a capillary tube

This example describes a gel prepared of crystalline endoglucanase (endo-1,4-β-glucanase, or 1,4-(1,3; 1,4)-β-D-Glucan 4-glucanohydrolase, EC 3.2.1.4, produced with Melanocarpus albomyces fermentation) and alginate, which can be run with small pressure through a very thin capillary (FIG. 13).

The gel was prepared by mixing three solutions together as follows:
1) 1 ml of 3% sodium alginate, as in the example 1
2) 2 ml of crystal suspension of endoglucanase (35 mg/ml) in 5 mM Na-acetate buffer pH 4.1

The solutions 1) and 2) were mixed together to a uniform crystal suspension.
3) 1 ml of 14 mM $CaCl_2$ was added to the above mixture gradually and mixing vigorously at the same time.

The crystal suspension prepared like this is gel-like and very stable. The crystals did not sediment on the bottom of the container during the 2 weeks observation period. Despite being gel-like the suspension can be easily stirred and pumped through a capillary tube. The gel turns into very fluid with minor stirring force. The suspension was pumped through a steel tube with the inner diameter of 0.48 mm and the length of 42 mm. When using the pressure of 200 millibars, the flow rate of 734 µl/min was achieved, which is 400 cm/min when converted to linear flow.

The mixture according to the example containing crystalline enzyme remains uniform suspension due to it being gel-like, but it is nevertheless efficiently and easily pumped through even a thin tube.

Example 86

This example is similar to the above example 85 in its embodiment. Only the CaCl$_2$ concentration was changed to higher:

The gel was prepared by mixing three solutions together as follows:
1) 1 ml of 3% sodium alginate
2) 2 ml of crystal suspension of endoglucanase (35 mg/ml) in 5 mM Na-acetate buffer pH 4.1

The solutions 1) and 2) were mixed together to a uniform crystal suspension.
3) 1 ml of 16 mM CaCl$_2$ was added to the above mixture gradually and mixing vigorously at the same time.

The crystal suspension prepared like this is gel-like and very stable like the suspension in the above example. However, this solution had higher viscosity than in the example 85, which becomes apparent in the capillary tube experiment. The suspension was pumped through a steel tube with the inner diameter of 0.48 mm and the length of 42 mm. When using the pressure of 200 millibars, the flow rate of 531 µl/min was achieved, which is 290 cm/min when converted to linear flow (FIG. 13).

Example 87

Concentrated Crystal Suspension in the Alginate Gel

An alginate gel was prepared by mixing 10 ml of 1.5% sodium alginate and 10 ml of 7 mM CaCl$_2$. The crystals of endoglucanase in 5 mM Na-acetate buffer pH 4.1 were filtered in vacuum filter so that all the free buffer solution was removed and a solid crystal mass was formed. The protein concentration of the crystal mass was 358.2 mg/1000 mg based on the dry-matter determination.

2.042 g of crystal mass of endoglucanase and 0.418 g of alginate gel were mixed together thoroughly. A uniform milk-like crystal suspension which was gel-like and very stable was prepared like this. The endoglucanase concentration of the mixture was determined to be 272 mg/ml. The concentration of alginate in the mixture was 0.14%. The suspension was pumped through a steel tube with the inner diameter of 0.48 mm and the length of 42 mm. When using the pressure of 198 millibars, the flow rate of 312 µl/min was achieved.

Example 88

Concentrated Crystal Suspension in the Alginate Gel 2.076 g of crystal mass of endoglucanase and 0.592 g of alginate gel were mixed together thoroughly as in the example 87. A uniform milk-like crystal suspension which was gel-like and very stable was prepared like this. The endoglucanase concentration of the mixture was determined to be 255 mg/ml. The concentration of alginate in the mixture was 0.18%. The suspension was pumped through a steel tube with the inner diameter of 0.48 mm and the length of 42 mm. When using the pressure of 208 millibars, the flow rate of 471 µl/min was achieved.

LITERATURE

1. Abel J (1926). Crystalline insulin. Proc. Natl. Acad. Sci. (Wash) 12, 132.
2. Bergfors, Terese M. (1999). In *Protein Crystallization*, (ed. Terese M. Bergfors), pp. 41-61. International university Line, La Jolla Calif.
3. Bodmeier R. Chen H, Paeratakul O. A novel approach to the oral delivery of micro- or nanoparticles. Pharmaceutical Research 1989; 6(5): 413-417. Abstract.
4. Bodmeier R, Paeratakul O. Spherical agglomerates of water-insoluble drugs. J Pharm Sci. 1989 November; 78(11):964-7. Abstract.
5. Borchard G, Junginger H E. Modern drug delivery applications of chitosan. Advanced Drug Delivery Reviews 2001; 52: 103.
6. Chenite A, Chaput C, Wang D, Combes C, Buschmann M D, Hoemann CD, Leroux J C, Atkinson B L, Binette F, Selmani A. Novel injectable neutral solutions of chitosan form biodegradable gels in situ. Biomaterials 2000 November; 21(21):2155-2161.
7. Desbrieres J. Viscosity of semiflexible chitosan solutions: influence of concentration, temperature, and role of intermolecular interactions. Biomacromolecules. 2002 March-April; 3(2):342-9.
8. Dornish M, Kaplan D, Skaugrud O. Standards and guidelines for biopolymers in tissue-engineered medical products: ASTM alginate and chitosan standard guides. American Society for Testing and Materials. Ann NY Acad Sci. 2001 November; 944:388-97.
9. Ducruix, A. and Giege, R. pp. 127-143. (1992). *Crystallization of Nucleic Acids and Proteins* Oxford University Press
10. el Fattah E A, Grant D J, Gabr K E, Meshali M M. Physical characteristics and release behavior of salbutamol sulfate beads prepared with different ionic polysaccharides. Drug Dev Ind Pharm. 1998 June; 24(6):541-7. Abstract.
11. Fernandez-Urrusuno R, Calvo P, Remunan-Lopez C, Vila-Jato J L, Alonso M J. Enhancement of nasal absorption of insulin using chitosan nanoparticles. Pharm Res. 1999 October; 16(10):1576-81. Abstract.
12. Gérentes P, Vachoud L, Doury J, Domard A. Study of a chitin-based gel as injectable material in periodontal surgery. Biomaterials 2002; 23: 1295-1302.
13. Hirano S. Chitin biotechnology applications. Biotechnol Annu Rev 1996; 2:237-58. Abstract.
14. Hoffman A S. Hydrogels for biomedical applications. Advanced Drug Delivery Reviews 2002; 43:3-12.
15. Huard L S, Qin J, Sun T, Bevemitz K J, Dutkiewicz J, Wallajapet P R R. Antimicrobial structures. 2001. Patent U.S. Pat. No. 6,197,322.
16. Janes K A, Calvo P, Alonso M J. Polysaccharide colloidal particles as delivery systems for macromolecules. Advanced Drug Delivery Reviews 2001; 47: 83-97.
17. Jumaa M, Furkert F H, Muller B W. A new lipid emulsion formulation with high antimicrobial efficacy using chitosan. Eur J Pharm Biopharm 2002 January; 53(1):115-23. Abstract.

18. Kim H J, Lee H C, Oh J S, Shin B A, Oh C S, Park R D, Yang K S, Cho C S. Polyelectroylte complex composed of chitosan and sodium alginate for wound dressing application. J Biomater Sci Polym Ed. 1999; 10(5):543-56. Abstract.
19. Kim T H, Park Y H, Kim K J, Cho C S. Release of albumin from chitosan-coated pectin beads in vitro. International Journal of Pharmaceutics 2003; 250: 371-383.
20. Kofuji K, Ito T, Murata Y, Kawashima S. Biodegradation and drug release of chitosan gel beads in subcutaneous air pouches of mice. Biol Pharm Bull 2001 24(2): 205-208.
21. Li J, Xu Z. Physical characterization of a chitosan-based hydrogel delivery system. J Pharm Sci. 2002 July; 91(7): 1669-77. Abstract.
22. van der Lubben I M, Verhoef J C, Borchard G, Junginger H E. Chitosan for mucosal vaccination. Advanced Drug Delivery Reviews 2001; 52: 139-144.
23. Margolin A L, Rakestraw S L, Khalaf N K, Shenoy B C, St Clair N L. Stabilized protein crystals, formulations comprising them and methods of making them. 2003. Patent US2003175239.
24. McPherson A. (1989). *Preparation and Analysis of Protein Crystals*. Robert E. Kriegler Publishing Company, Malabar, Fla.
25. Mierisch C M, Jordan L C, Balian G, Diduch D R. The use of calcium alginate in the treatment of articular cartilage defects. 47th Annual Meeting, Orthopaedic Research Society, Feb. 25-28, 2001, San Francisco Calif. Poster.
26. Miyazaki S, Kubo W, Attwood D. Oral sustained delivery of theophylline using in-situ gelation of sodium alginate. Journal of Controlled Release 2000; 67: 275-280.
27. Robert, M. C. and Lefauchcheux, F. (1988). J. Cryst. Growth, 90, 358-367.
28. Robert, M. C., Provost, K. and Lefauchcheux, F. (1992). Crystallization in Gels and Related Methods. *Crystallization of Nucleic Acids and Proteins*, edited by A. Ducruix and R. Giege, pp. 127-143. Oxford University Press.
29. Sakurada T. Composite raw material comprising chitosan and protein material. 1995. Patent JP7258972. Abstract.
30. Schlichtkrull J (1956). Insulin crystals. II. Shape of rhombohedral zinc-insulin crystals in relation to species and crystallization media. Acta Chem. Scand. 10, 1459.
31. Schlichtkrull J (1960). Insulin crystal suspensions having a protracted effect. Patent no. GB835638.
32. Schmidt R J. Therapeutic compositions comprising modified polysaccharides. 2003. Patent WO03080135 (GB2386900), abstract.
33. Scott D A (1934). CCXI. Crystalline insulin. Biochem. J. 28, 1592.
34. Serp D, Cantana E, Heinzen C, von Stockar U, Marison I W. Characterization of an encapsulation device for the production of monodisperse alginate beads for cell immobilization. Biotechnology and bioengineering 2000 Oct. 5; 70(1): 41-53.
35. Singla A K, Chawla M. Chitosan: some pharmaceutical and biological aspects—an update. Journal of Pharmacy and Pharmacology 2001; 53: 1047-1067.
36. Säkkinen M, Marvola M. A peroral pharmaceutical formulation for controlled release of a drug. 2001. Patent WO0176562.
37. Takeuchi H, Yamamoto H, Kawashima Y. Mucoadhesive nanoparticulate systems for peptide drug delivery. Advanced Drug Delivery Reviews 2001; 47: 39-54.
38. Takeuchi H, Yasuji T, Yamamoto H, Kawashima Y. Spray-dried lactose composite particles containing an ion complex of alginate-chitosan for designing a dry-coated tablet having a time-controlled releasing function. Pharmaceutical Research 2000; 17(1): 94-99. Abstract.
39. Takka S and Acartürk F. Calcium alginate microparticles for oral administration: I: effect of sodium alginate type on drug release and drug entrapment efficiency. J Microencapsulation 1999; 16(3): 275-90.
40. Thanou M, Verhoef J., Junginger H. Oral drug absorption enhancement by chitosan and its derivatives. Advanced Drug Delivery Reviews 2001; 52: 117-126.
41. Tiourina O. and Sukhorukov G. Multilayer alginate/protamine microsized capsules: encapsulation of α-chymotrypsin and controlled release study. International Journal of Pharmaceutics 2002; 242: 155-161.
42. Tonnesen H., Karlsen J. Alginate in drug delivery systems. Drug Dev Ind Pharm 2002 July; 28(6): 621-30. Abstract.
43. Ueno H, Mori T, Fujinaga T. Topical formulations and wound healing applications of chitosan. Advanced Drug Delivery Reviews 2001; 52: 105-115.
44. Visuri, K.(1987) U.S. Pat No. 4,699,882 Stable glucose isomerase concentrate and a process for the preparation of thereof
45. Visuri, K. (1992) U.S. Pat. No. 5,120,650 Method for producing crystalline glucose isomerase
46. Vuolanto, A.; Uotila, S.; Leisola, M.; Visuri, K. (2003) Solubility and crystallization of xylose isomerase from *Streptomyces rubiginosus*, J. Cryst. Growth 257:403-411.
47. Xue C, Yu G, Hirata T, Terao J, Lin H. Antioxidative activities of several marine polysaccharides evaluated in a phosphatidylcholine-liposomal suspension and organic solvents. Biosci Biotechnol Biochem. 1998 February; 62(2):206-9. Abstract.
48. Törrönen, A., Harkki, A. and Rouvinen, J. (1994) Three-dimensional structure of endo-1,4-β-xylanase II from *Trichoderma reesei*: two conformational states in the active site. The EMBO Journal Vol. 13, no. 11, pp. 2493-2501

What is claimed is:

1. A method for crystallization of proteins and peptides, wherein (a) a protein solution or a peptide solution, in which the solvent is water, and (b) a polymer solution, in which alginate or dextrin or chitosan or pectin or hydrolysate of any above mentioned polymer or a mixture of any above mentioned polymer is dissolved in water, are prepared and that the prepared solutions (a) and (b) are mixed together and that after the combining the protein or the peptide crystallizes permanently.

2. The method according to claim 1, wherein the crystallizing polymer solution contains alginate or a gel thereof 8% or less.

3. The method according to claim 1, wherein the crystallizing polymer solution contains dextrin 30% or less.

4. The method according to claim 1, wherein the crystallizing polymer solution contains chitosan or a gel thereof 1% or less.

5. The method according to claim 1, wherein the crystallizing polymer solution contains pectin or a gel thereof 9% or less.

6. The method according to claim 1, wherein the crystallizing solution is a mixture of two or more of the polymers.

7. The method according to claim 1, wherein the crystallizing polymer is hydrolyzed.

8. The method according to claim 1, wherein the crystallization occurs either under stirring or without stirring within 1-7 days.

9. The method according to claim 1, wherein it can be used for preparing crystals, the size of which is 1-100 micrometers.

10. The method according to claim 1, wherein by stirring continuously during the crystallization very small crystals can be prepared, the size of which is in the range of 1-10 micrometers.

11. The method according to claim 1, wherein the protein or the peptide crystallized like this may float freely as uniform suspension, which can be fed with moderate pressure through a capillary.

* * * * *